United States Patent [19]
Babiak et al.

[11] Patent Number: 5,939,435
[45] Date of Patent: Aug. 17, 1999

[54] 2-SUBSTITUTED-1-ACYL-1,2-DIHYDROQUINOLINE DERIVATIVES

[75] Inventors: John Babiak, Martinsville, N.J.; Hassan Mahmoud Elokdah, Yardley, Pa.; Christopher Paul Miller; Theodore Sylvester Sulkowski, both of Wayne, Pa.

[73] Assignee: American Home Products Corporation, Madison, N.J.

[21] Appl. No.: 09/015,178

[22] Filed: Jan. 29, 1998

Related U.S. Application Data

[60] Provisional application No. 60/037,409, Feb. 3, 1997.

[51] Int. Cl.$^6$ .......................... A61K 31/47; C07D 215/14
[52] U.S. Cl. ..................... 514/311; 546/168; 546/169
[58] Field of Search .................................. 546/176, 168, 546/169; 514/311

[56] References Cited

FOREIGN PATENT DOCUMENTS 9216508  10/1992  WIPO .

OTHER PUBLICATIONS

Walters, LR et al. J. Chem. Eng. Data 16(1), 115–17, 1971.

Popp and Soto, J. Chem. Soc. 1963, 1760–1763.

Popp, "Reissert Compounds and Related N–Acyldihydroquinolines," Quinolines, Part II, (1982), John Wilen & Sons, Ltd., pp. 353–375.

Cobb and McEwen, J. Amer. Chem. Soc., 77, 5042–5048 (1955).

Walters et al., J. Het. Chem. 5, 577–578, 1968.

*Primary Examiner*—Evelyn Mei Huang
*Attorney, Agent, or Firm*—Michael R. Nagy

[57] ABSTRACT

This invention relates to the use of 2-substituted-1-acyl-1,2-dihydroquinoline derivatives to increase high density lipoprotein cholesterol (HDL-C) concentration and as therapeutic compositions for treating atherosclerotic conditions such as dyslipoproteinamias and coronary heart disease.

2 Claims, No Drawings

2-SUBSTITUTED-1-ACYL-1,2-DIHYDROQUINOLINE DERIVATIVES

This appplication claims the benefit of priority to provisional patent application No. 60/037,409 filed on Feb. 3, 1997.

FIELD OF INVENTION

This invention relates to the use of 2-substituted-1-acyl-1,2-dihydroquinoline derivatives to increase high density lipoprotein cholesterol (HDL-C) concentration and as therapeutic compositions for treating atherosclerotic conditions such as dyslipoproteinamias and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.,* 11 (1951) 480–493; Gofman et al., *Circulation,* 34 (1966) 679–697; Miller and Miller, *Lancet,* 1 (1975) 16–19; Gordon et al., *Circulation,* 79 (1989) 8–15; Stampfer et al., *N. Engl. J. Med.,* 325 (1991) 373–381; Badimon et al., *Lab. Invest.,* 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles appears to be correlated with a decrease in the number of sites of stenosis in the coronary arteries of humans (Miller et al, *Br. Med. J.,* 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis,* 6 (1986) 434–441). Data of this nature suggests that one antiatherogenic property of HDL may lie in its ability to deplete tissues of excess free cholesterol and eventually lead to the delivery of this cholesterol to the liver (Glomset, *J. Lipid Res.,* 9 (1968) 155–167). This has been supported by experiments showing efficient transfer of cholesterol from HDL to the liver (Glass et al, *Circulation,* 66 (*Suppl. II*) (1982) 102; MacKinnon et al., *J. Biol. Chem.,* 261 (1986) 2548–2552). In addition, HDL may serve as a reservoir in the circulation for apoproteins necessary for the rapid metabolism of triglyceride-rich lipoproteins (Grow and Fried, *J. Biol. Chem.,* 253 (1978) 1834–1841; Lagocki and Scanu, *J. Biol. Chem.,* 255 (1980) 3701–3706; Schaefer et al., *J. Lipid Res.,* 23 (1982) 1259–1273). Accordingly, agents which increase HDL cholesterol concentrations are useful as anti-atherosclerotic agents, particularly in the treatment of dyslipoproteinemias and coronary heart disease.

SUMMARY OF THE INVENTION

In accordance with this invention there is provided a group of 2-substituted-1-benzoyl-1,2-dihydroquinolines useful for increasing HDL-C concentration in the blood of a mammal according to the formula

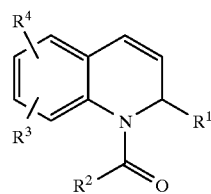

wherein:
R$^1$ is carboxamide [—C(O)NH$_2$] or carboxamidoxime [—C(=NOH)NH$_2$];
R$^2$ is phenyl optionally substituted with one to three groups selected from halogen, alkyl of 1–6 carbon atoms, or perfluoroalkyl of 1–6 carbon atoms; and
R$^3$ and R$^4$ are hydrogen, halogen, C$_1$–C$_6$ alkyl or trifluoromethyl.

The most preferred HDL-C elevating compounds of this invention are:
1-(benzoyl)-1,2-dihydro-quinoline-2-carboxylic acid amide,
1-(benzoyl)-6-chloro-1,2-dihydro-quinoline-2-carboxylic acid amide,
1-(4-fluorobenzoyl)-1,2-dihydro-quinoline-2-carboxylic acid amide,
[1-(4-trifluoromethylbenzoyl)-1,2-dihydro-quinolin-2-yl]-N-hydroxy-methanimidamide,
[1-(4-fluorobenzoyl)-1,2-dihydro-quinolin-2-yl]-N-hydroxy-methanimidamide, and
[1-(benzoyl)-1,2-dihydro-quinolin-2-yl]-N-hydroxy-methanimidamide.

The novel compounds of this invention are those having the formula

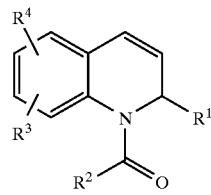

wherein:
R$^1$ is carboxamide [—C(O)NH$_2$] or carboxamidoxime [—C(=NOH)NH$_2$];
R$^2$ is phenyl optionally substituted with one to three groups selected from halogen, alkyl of 1–6 carbon atoms, or perfluoroalkyl of 1–6 carbon atoms;
R$^3$ and R$^4$ are hydrogen, halogen, C$_1$–C$_6$ alkyl or trifluoromethyl;
with a proviso that when R$^1$ is carboxamide, either R$^2$ is substituted as defined above or R$^3$ and R$^4$ are not both hydrogen;
and a further proviso that when R$^1$ is carboxamidoxime, R$^3$ and R$^4$ are not H or F.

DETAILED DESCRIPTION OF THE INVENTION

The compounds of the invention can be prepared readily according to the following reaction scheme or modification thereof using readily available starting materials, reagents and conventional synthetic procedures. It is also possible to make use of variants of these process steps, which in themselves are known to and well within the preparatory skill of the medicinal chemist.

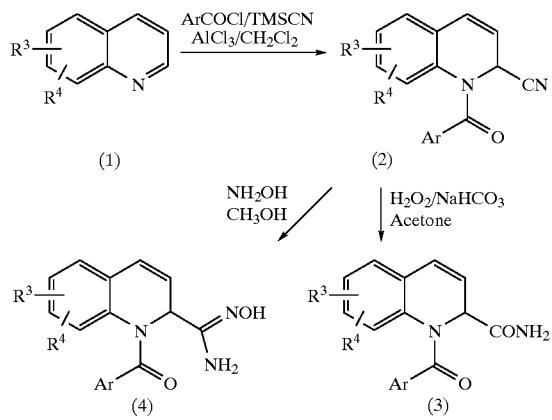

1-Acyl-1,2-dihdro-quinoline-2-carbonitrile (2) was prepared by reaction of one part quinoline (1), 1.3 parts of an acid chloride (ArCOCl), 1.3 parts of trimethylsilyl cyanide (TMSCN), and a catalytic amount of aluminum chloride. The reaction was carried out at ambient temperature for a period of 0.5 to 4 hours in a solvent such as methylene chloride. The carboxamide (3) is prepared by reaction of the nitrite (2) with 30% hydrogen peroxide (excess) in acetone in presence of a base such as sodium bicarbonate at ambient temperature for a period of 4 hours. Reaction of the nitrite (2) with hydroxyl amine (excess) in methanol for 18 hours at ambient temperature afforded the corresponding amidoxime (4).

The following representative examples are included to illustrate the methods of preparation of invention compounds and are not to be considered as limiting to this disclosure in any way. Still other methods may be apparent to those skilled in the art of organic medicinal chemistry.

EXAMPLE 1

Step 1

1-(Benzoyl)-1,2-dihydro-quinoline-2-carbonitrile

A mixture of quinoline (19.35 g), benzoyl chloride (28.1 g), aluminum chloride (1.0 g) and methylene chloride (500 mL) was stirred at ambient temperature for 10 minutes. Trimethyl silyl cyanide (20.0 g) was added dropwise. The stirring was continued for 4 hours. The mixture was washed twice with 1N HCl (500 mL) then with water (500 mL). The organic phase was dried over anhydrous magnesium sulfate then evaporated to dryness. The title compound (26.0 g) was obtained as a white solid, m.p. 153–154° C. This product was used for the preparation of the title compound described in step 2, and for preparation of the title compound described in Example 2.

Step 2

1-(Benzoyl)-1,2-dihydro-quinoline-2-carboxylic acid amide 1-(Benzoyl)-1,2-dihydro-quinoline-2-carbonitrile (26.0 g) was dissolved in acetone (500 mL). Solid sodium bicarbonate (15 g) was added. The mixture was stirred for 30 minutes. 30% Hydrogen peroxide solution (250 mL of a 30% solution) was added drop-wise. After stirring for 4 hours, the acetone was evaporated under vacuum. The residue was acidified with 1N HCl. The precipitate was collected, washed with water and air dried. The solid was slurried in ether then filtered. The title compound (15.3 g) was obtained as an off-white solid, m.p. 169–171° C.

Anal. for $C_{17}H_{14}N_2O_2 \cdot \frac{1}{4}H_2O$: Calc'd: C, 72.20; H, 5.17; N, 9.91, Found: C, 72.58; H, 5.01; N, 9.89. Mass spectrum (CI, $[M+H]^+$) m/z 279.

EXAMPLE 2

[1-(Benzoyl)-1,2-dihydro-quinolin-2-yl]-N-hydroxy-methanimidamide

Hydroxyl amine hydrochloride (3.2 g) and sodium methoxide (4.45 g) were stirred in methanol (40 mL) while cooling in ice. After 20 minutes, the mixture was filtered. The filtrate was added to a solution of 1-(benzoyl)-1,2-dihydro-quinoline-2-carbonitrile (7.8 g) in methanol (45 mL). The mixture was stirred for 18 hours then concentrated to one half volume. The solid was collected, washed with ether and dried to give the title compound (5.8 g) as a white solid, m. p. 176–178° C.

Anal. for $C_{17}H_{15}N_3O_2$: Calc'd: C, 69.61; H, 5.16; N, 14.33, Found: C, 69.89; H, 4.99; N, 14.03. Mass spectrum (EI, $M^+$) m/z 293.

EXAMPLE 3

Step 1

1-(4-Fluorobenzoyl)-1,2-dihydro-quinoline-2-carbonitrile

The title compound was prepared by the procedure described in step 1 of Example 1 using 13.0 g of quinoline, 39.0 g of 4-fluorobenzoyl chloride, 0.1 g of aluminum chloride, 30.0 g of trimethyl silyl cyanide, and 500 mL of methylene chloride. The title compound (42.0 g) was obtained as a solid, m. p. 111–113° C. This product was used for the preparation of the title compound described in step 2, and for preparation of the title compound described in Example 4.

Step 2

1-(4-Fluorobenzoyl)-1,2-dihydro-quinoline-2-carboxylic acid amide 1-(4-Fluorobenzoyl)-1,2-dihydro-quinoline-2-carbonitrile (24.0 g) was dissolved in acetone (500 mL). Solid sodium bicarbonate (15 g) was added. The mixture was stirred for 10 minutes. 30% Hydrogen peroxide solution (300 mL of a 30% solution) was added drop-wise. Stirring was continued for 30 minutes. The mixture was then warmed slowly until a solution formed, then stirred at ambient temperature for 2 hours. The acetone was evaporated under vacuum. The aqueous residue was diluted with water (100 mL), and acidified with 1N HCl. The mixture was extracted with ethyl acetate (500 mL). The organic extract was washed with water (300 mL), dried over anhydrous sodium sulfate, then concentrated. Hexane was added to the precipitation point. The solid was collected and dried to give the title compound as a white solid, m. p. 149–151° C.

Anal. for $C_{17}H_{13}FN_2O_3$: Calc'd: C, 68.91; H, 4.42; N, 9.45, Found: C, 68.54; H, 4.32; N, 9.19. Mass spectrum (DCI, $[M+H]^+$) m/z 297.

EXAMPLE 4

[1-(4-Fluorobenzoyl)-1,2-dihydro-quinolin-2-yl]-N-hydroxy-methanimidamide

The title compound was prepared by the procedure described in Example 2 using 1-(4-flurobenzoyl)-1,2-dihydro-quinoline-2-carbonitrile (7.8 g). Crystallization from ethyl acetate afforded the title compound (5.1 g) as a white solid, m. p. 174–175° C.

Anal. for $C_{17}H_{14}FN_3O_2$: Calc'd: C, 65.59; H, 4.53; N, 13.50, Found: C, 65.30; H, 4.39; N, 14.35. Mass spectrum (EI, M$^+$) m/z 311.

EXAMPLE 5

Step 1

1-(4-Trifluoromethylbenzoyl)-1,2-dihydro-quinoline-2-carbonitrile

The title compound was prepared by the procedure described in step 1 of Example 1 using 13.0 g of quinoline, 32.0 g of 4-trifluoromethylbenzoyl chloride, 0.5 g of aluminum chloride, 14.8 g of trimethyl silyl cyanide, and 500 mL of methylene chloride. Crystallization from diethyl ether/hexane afforded the title compound (28.0 g) as a white solid, m. p. 149–151° C. This product was used for the preparation of the title compound described in step 2, and for preparation of the title compound described in Example 6.

Step 2

1-(4-Trifluoromethylbenzoyl)-1,2-dihydro-quinoline-2-carboxylic acid amide

The title compound was prepared by the procedure described in step 2 of Example 1 using 20.0 g of 1-(4-Trifluoromethylbenzoyl)-1,2-dihydro-quinoline-2-carbonitrile, 10.0 g of sodium bicarbonate, 500 mL of acetone, and 250 mL of 30% hydrogen peroxide solution. Crystallization from acetonitrile afforded the title compound (8.6 g) as a white solid, m. p. 158–160° C.

Anal. for $C_{18}H_{13}F_3N_2O_2 \cdot \frac{1}{3}H_2O$: Calc'd: C, 61.37; H, 3.91; N, 7.95, Found: C, 61.24; H, 3.78; N, 7.81. Mass spectrum (DCI, [M+H]$^+$) .m/z 347.

EXAMPLE 6

[1-(4-Trifluoromethylbenzoyl)-1,2-dihydro-quinolin-2-yl]-N-hydroxy-methanimidamide The title compound was prepared by the procedure described in of Example 2 using 1-(4-fluoromethylbenzoyl)-1,2-dihydro-quinoline-2-carbonitrile (9.84 g). Crystallization from ether/hexane afforded the title compound (8.5 g) as a white solid, m. p. 152–154° C.

Anal. for $C_{18}H_{14}F_3N_3O_2$: Calc'd: C, 59.83; H, 3.90; N, 11.63, Found: C, 59.65; H, 3.67; N, 11.57. Mass spectrum (EI, M$^+$) .m/z 361.

EXAMPLE 7

Step 1

1-(Benzoyl)-6-chloro-1,2-dihydro-quinoline-2-carbonitrile

A solution of 6-chloroquinoline (9.5 g), benzoyl chloride (13.2 g) in methylene chloride (50 mL) was treated with AlCl$_3$ (0.10 g) followed by dropwise addition of trimethyl silyl cyanide (12.5 mL). After 0.5 hour, the mixture was diluted with 150 mL of methylene chloride and washed with water, 1N HCl, saturated sodium bicarbonate (aq.), and brine. The organic phase was dried over magnesium sulfate then evaporated to dryness. The residue was purified by column chromatography on silica gel using ethyl acetate/hexane (3:7) as the eluting solvent. The title compound (13 g) was obtained as a white solid, m.p. 141–143° C. This product was used for the preparation of the title compound described in step 2.

Step 2

1-(Benzoyl)-6-chloro-1,2-dihydro-quinoline-2-carboxylic acid amide

A solution of 1-(Benzoyl)-6-chloro-1,2-dihydro-quinoline-2-carbonitrile (8.0 g), sodium bicarbonate (4.0 g), and 0.1N aqueous sodium hydroxide (20 mL) in acetone (125 mL) was treated with slow addition of 30% hydrogen peroxide (120 mL). The pH of the reaction was kept near 8 by the addition of 0.1N sodium hydroxide. After 4 hours, the mixture was diluted with ethyl acetate and washed with an aqueous solution of sodium thiosulfate. The organic phase was subsequently washed with water and brine. The organic phase was dried over magnesium sulfate and evaporated to dryness. The residue was chromatographed on silica gel using ethyl acetate/hexane (2:8) followed by ethyl acetate/methylene chloride/hexane (3:1:6) and finally 100% ethyl acetate to yield 1.5 g of the desired compound as a white solid, m.p. 230–234° C.

Anal. for $C_{17}H_{13}ClN_2O_2 \cdot \frac{1}{4}H_2O$: Calc'd: C, 64.36; H, 4.29; N, 8.83, Found: C, 64.74; H, 4.33; N, 8.81. Mass spectrum (DCI, [M+H]$^+$) .m/z 313.

Pharmacology

The ability of the compounds of this invention to increase blood serum HDL levels was established by the following standard experimental procedure for determination of HDL cholesterol:

Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Sigma Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25 C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 ul of serum is injected onto Superose 12 and Superose 6 (Pharmacia), in series, with a column buffer of 0.05M Tris (2-amino-2-hydroxymethyl-1,3-propanediol) and 0.15M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45 C. The eluent is monitored by measuring absorbance at 490 nm and gives a continuous absorbance signal proportional to the cholesterol concentration. The relative concentration of each lipoprotein class is calculated as the percent of total absorbance. HDL cholesterol concentration, in serum, is calculated as the percent of total cholesterol as determined by FPLC multiplied by the total serum cholesterol concentration.

The compounds of the present invention increase HDL cholesterol concentrations as summarized in Table I:

TABLE I

| Compound of Example | Dose (mg/kg/day) | Duration of treatment (days) | HDL Cholesterol Level Increase (%) |
|---|---|---|---|
| 1 | 100 | 8 | 139 |
| 2 | 100 | 8 | 77 |
| 3 | 50 | 8 | 74 |
| 4 | 100 | 8 | 57 |
| 5 | 100 | 8 | 23 |
| 6 | 100 | 8 | 46 |
| 7 | 50 | 8 | 32 |

Pharmaceutical Composition

This invention also provides pharmaceutical compositions comprised of the 2-substituted-1-acyl-1,2-dihydroquinoline derivatives either alone or in combination with excipients (i.e. pharmaceutically acceptable materials with no pharmcological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 10 to about 2000 milligrams/kilogram per day. However, in general, satisfactory results are indicated to be obtained at daily dosages in the range of from 400 milligrams to about 2000 milligrams, conveniently administered in divided doses two to four times a day.

What is claimed is:

1. A method of elevating high density lipoprotein in a mammal which comprises administration to a mammal in need thereof of a therapeutically effective amount of a compound having the formula

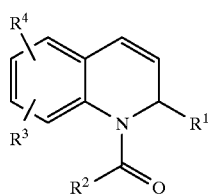

wherein:

$R^1$ is carboxamide [—C(O)NH$_2$] or carboxamidoxime [—C(=NOH)NH$_2$];

$R^2$ is phenyl optionally substituted with one to three groups selected from halogen, alkyl of 1–6 carbon atoms, or perfluoroalkyl of 1–6 carbon atoms;

$R^3$ and $R^4$ are hydrogen, halogen, $C_1$–$C_6$ alkyl or trifluoromethyl.

2. The method according to claim 1 wherein the therapeutically effective compound is selected from:

1-(benzoyl)-1,2-dihydro-quinoline-2-carboxylic acid amide, 1-(benzoyl)-6-chloro-1,2-dihydro-quinoline-2-carboxylic acid amide, 1-(4-fluorobenzoyl)-1,2-dihydro-quinoline-2-carboxylic acid amide,

[1-(4-trifluoromethylbenzoyl)-1,2-dihydro-quinolin-2-yl]-N-hydroxy-methanimidamide,

[1-(4-fluorobenzoyl)-1,2-dihydro-quinolin-2-yl]-N-hydroxy-methanimidamide, and

[1-(benzoyl)-1,2-dihydro-quinolin-2-yl]-N-hydroxy-methanimidamide.

* * * * *